United States Patent [19]
Giebeler

[11] Patent Number: 4,919,537
[45] Date of Patent: Apr. 24, 1990

[54] UV SCANNING SYSTEM FOR CENTRIFUGE

[75] Inventor: Robert Giebeler, Cupertino, Calif.

[73] Assignee: Beckman Instruments Inc., Fullerton, Calif.

[21] Appl. No.: 309,507

[22] Filed: Feb. 10, 1989

Related U.S. Application Data

[63] Continuation-in-part of Ser. No. 115,023, Oct. 29, 1987, Pat. No. 4,830,493.

[51] Int. Cl.$^5$ .............................. G01J 3/24; G01J 3/42
[52] U.S. Cl. ..................... 356/328; 250/373; 356/334; 356/427
[58] Field of Search .................. 356/328, 334, 427; 250/373; 494/10

[56] References Cited

U.S. PATENT DOCUMENTS

| | | |
|---|---|---|
| 3,628,849 | 12/1971 | Flamand . |
| 3,652,860 | 3/1972 | Walker . |
| 3,712,742 | 1/1973 | Cohen . |
| 3,721,487 | 3/1973 | Pieuchard et al. . |
| 3,807,874 | 4/1974 | Gropper . |
| 3,909,134 | 9/1975 | Pieuchard et al. . |
| 3,930,728 | 1/1976 | Pieuchard et al. . |
| 3,942,048 | 3/1976 | Laude et al. . |
| 3,973,850 | 8/1976 | Pouey . |

FOREIGN PATENT DOCUMENTS

647598A5 1/1980 Switzerland .

Primary Examiner—F. L. Evans
Attorney, Agent, or Firm—William H. May; Paul R. Harder

[57] ABSTRACT

A centrifuge sample is optically scanned during centrifuging. The sample, placed in a centrifuge rotor having a cell with top and bottom windows, is spun until stratification and discrete layering occurs within the sample. Such layering occurs on layers that are precisely normal to the radius of the centrifuge at the point of sample and parallel to the spin axis of the centrifuge. A slit scanner having a slit normal to the sample plane transverses the width of the sample below the cell to detect with precision the precise location of the strata in the cell. A light source is reflected by a toroidal mirror having two radius of curvature. One radius of curvature is selected to collimate rays of light parallel to the layer of the sample. The mirror is ruled with respect to the other radius of curvature to chromatically classify light to preselect band width. Rotation of the mirror preserved collimation but enables selected scanning light frequency.

7 Claims, 6 Drawing Sheets

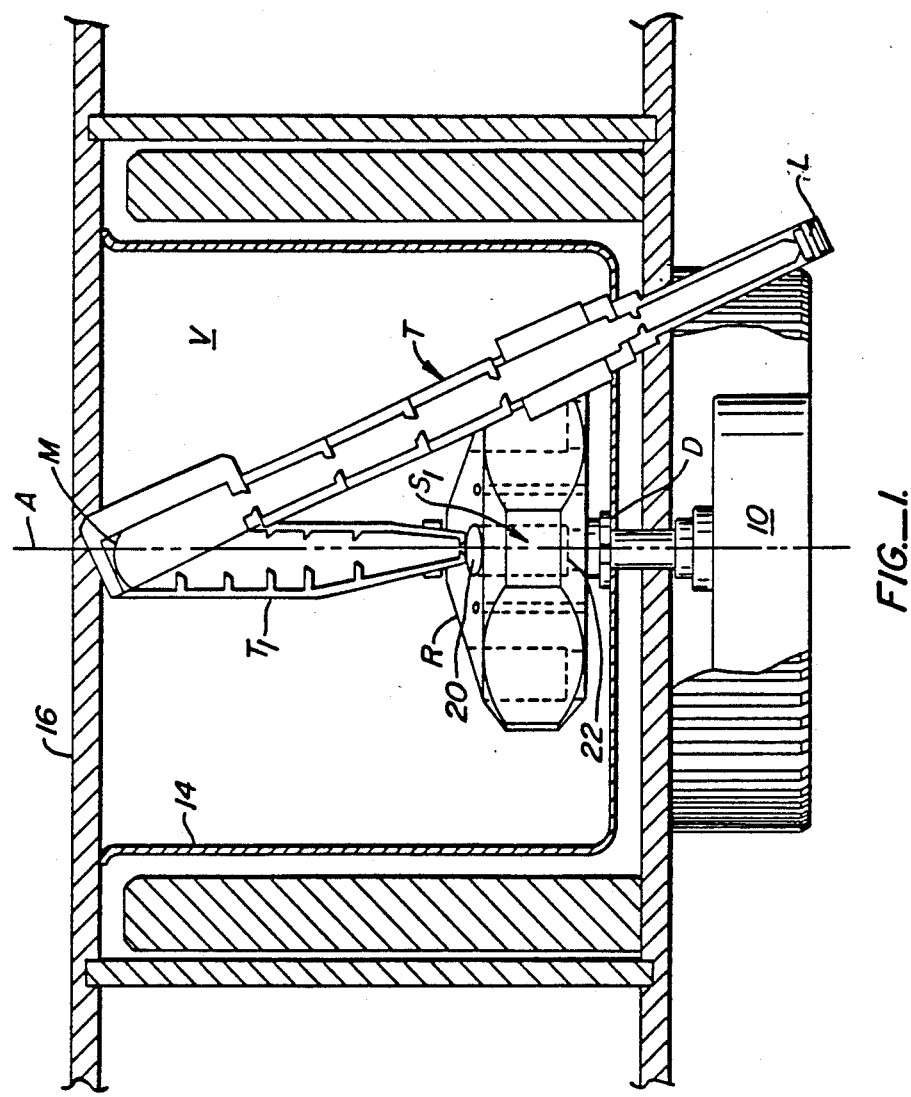

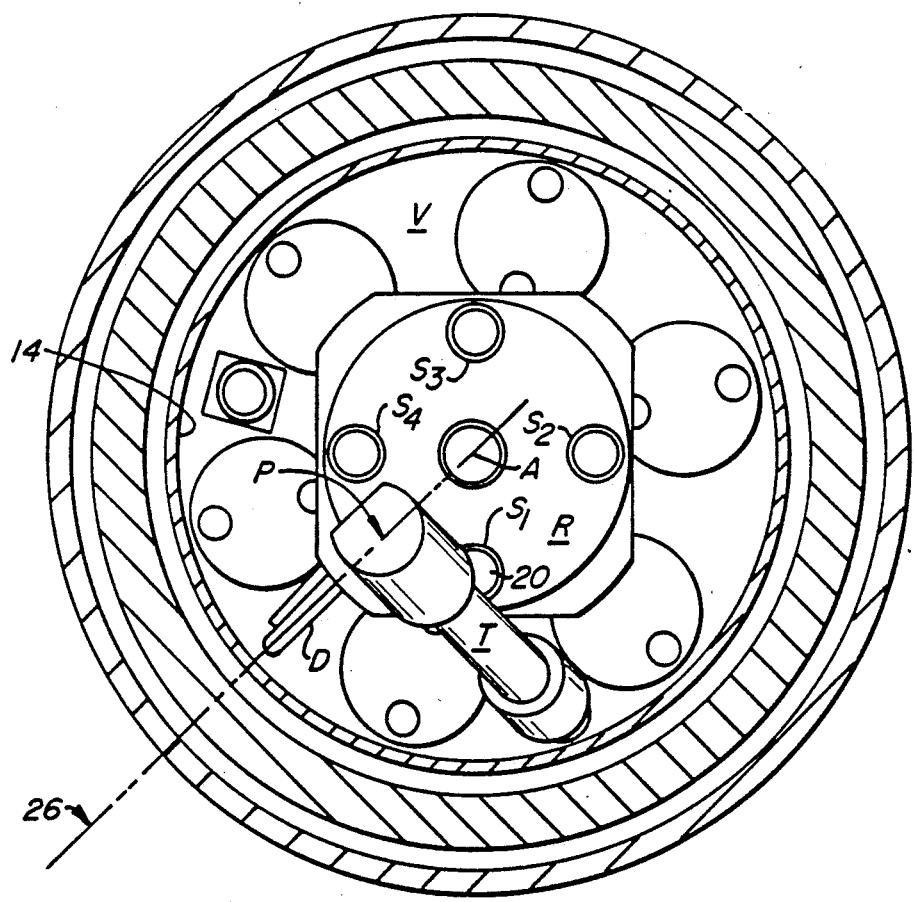
FIG._2.

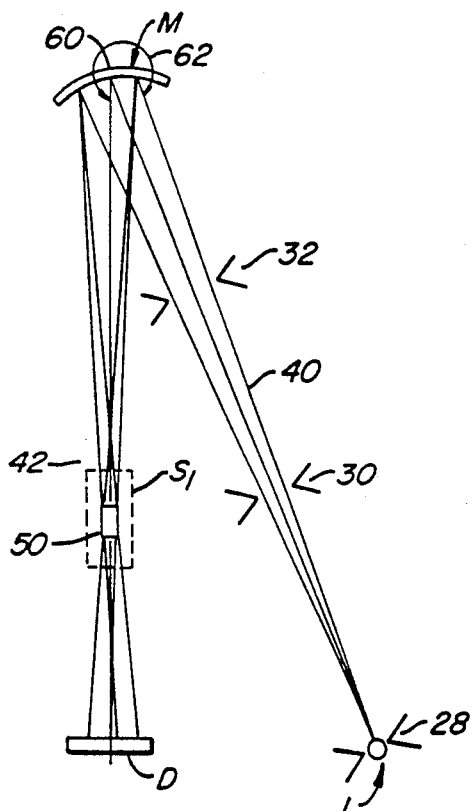
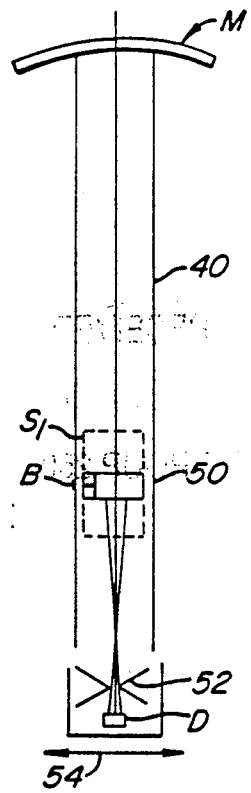
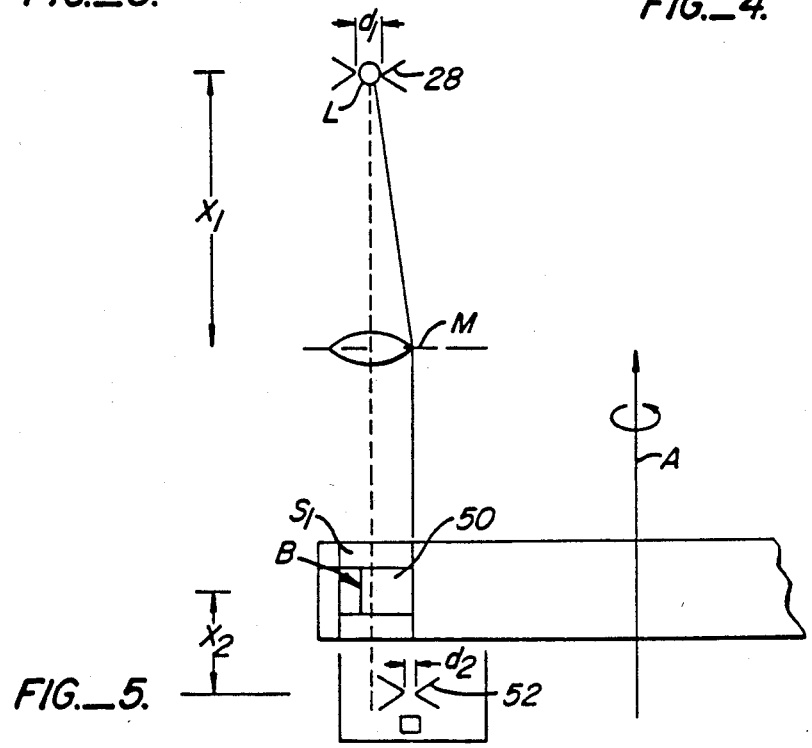
FIG._3.
FIG._4.
FIG._5.

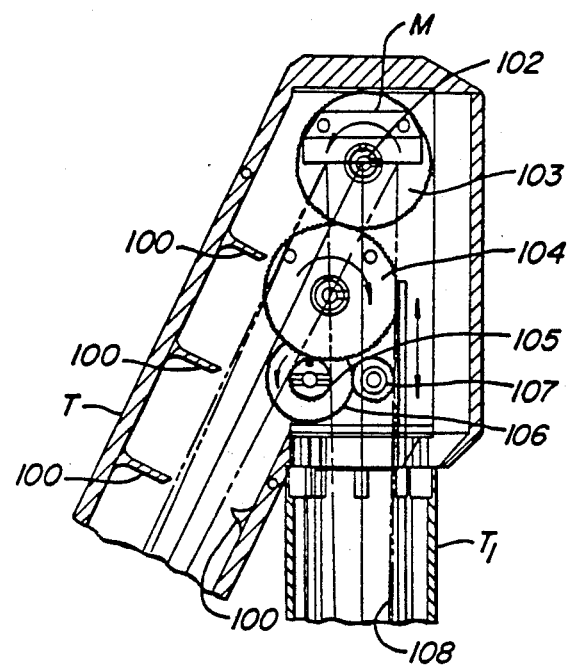
FIG._6.

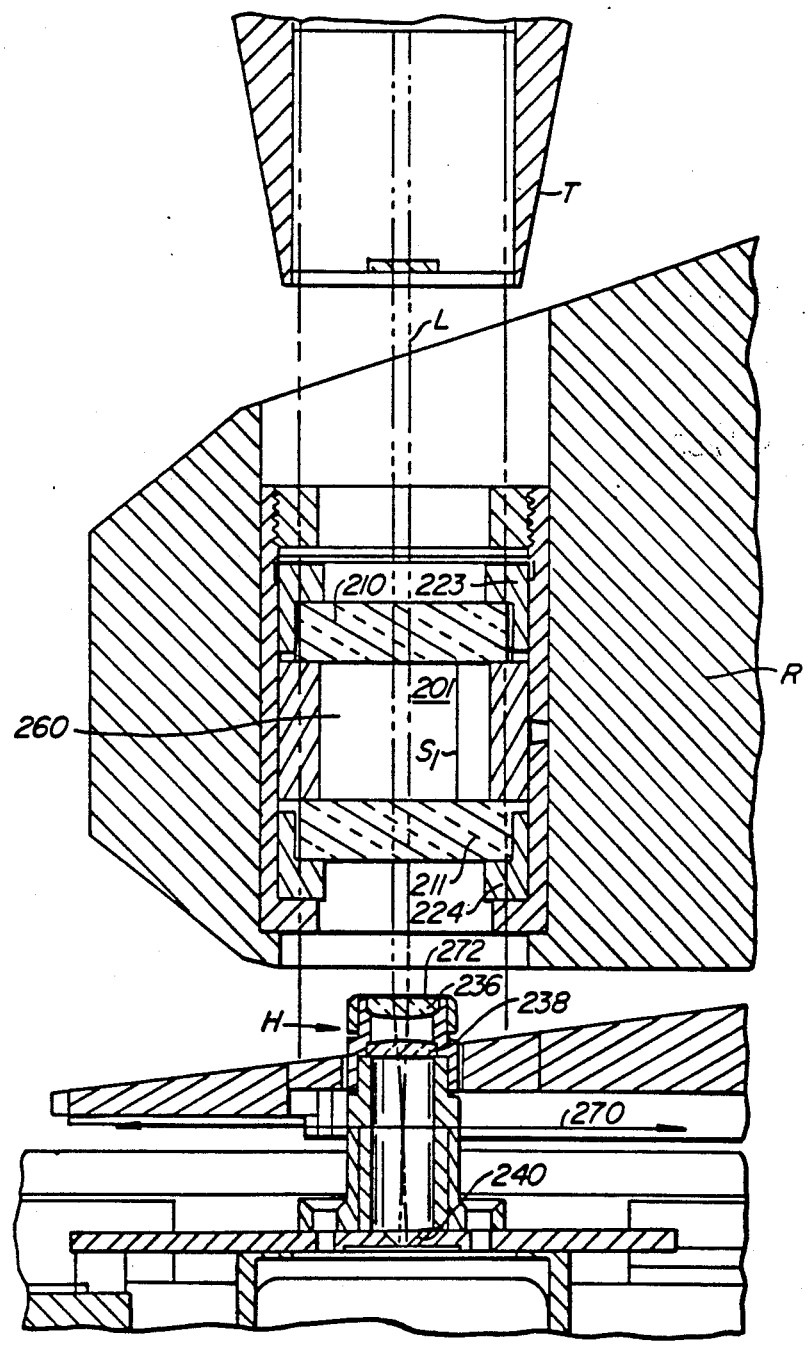
FIG._7.

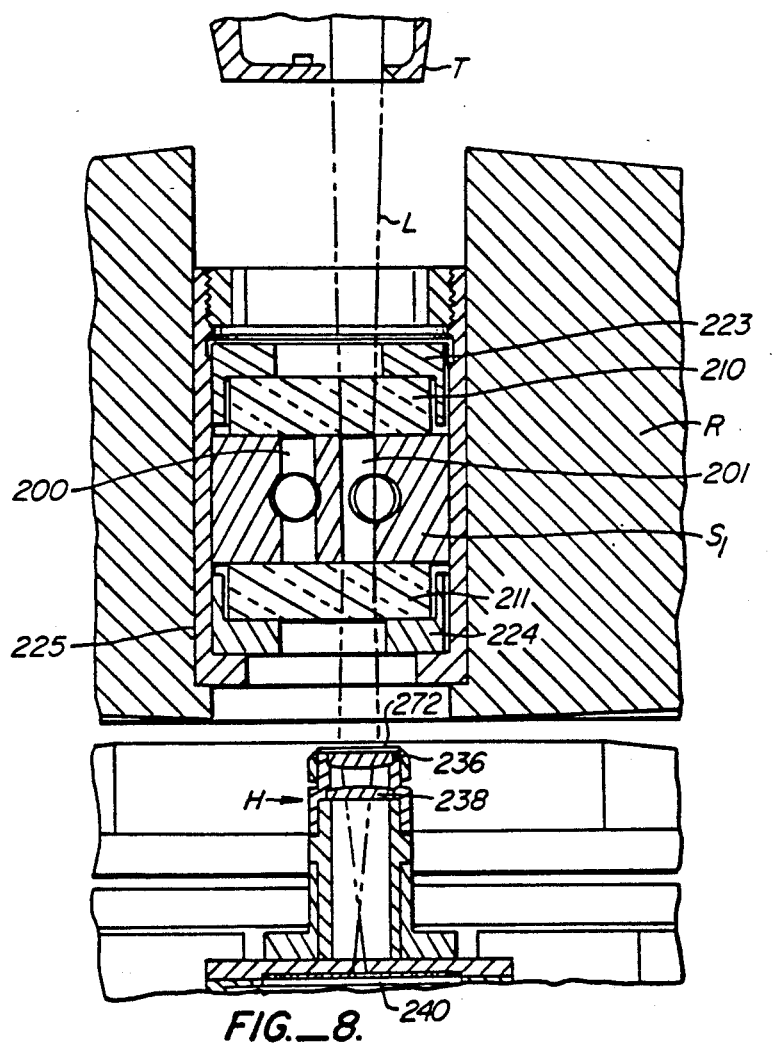
FIG._8.
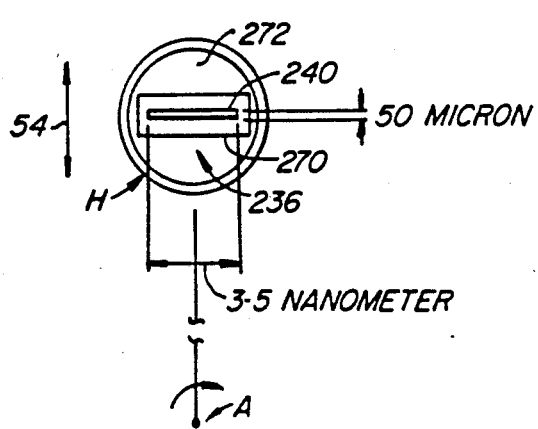
FIG._9.

UV SCANNING SYSTEM FOR CENTRIFUGE

BACKGROUND OF THE INVENTION

This application is a continuation-in-part-of Ser. No. 07/115,023, filed Oct. 29, 1987, now U.S. Pat. No. 4,830,493.

This invention relates to centrifuges. In particular this invention relates to an optical scanning system for dynamically tracking the progress of stratification within a sample while the centrifuging process occurs.

SUMMARY OF THE PRIOR ART

It is known to provide a centrifuge rotor with a sample cell and to observe the sample cell while centrifuging occurs. Specifically, and in the prior art, a light source has been collimated. The collimated light impinges downwardly through the sample cell through upper and lower windows. The collimated light passes precisely parallel to planes of sample stratification at the sample point. The imaging system refocuses, the sample image into plane of a scanning slit. The light passes through an interference filter as it passes to the scanning slit. A photodetector immediate the scanning slit enables detection of bands dynamically while centrifuging is underway.

It is known to collimate light parallel to the radius of a spinning rotor only. This can increase the light intensity at the sample and allows the strata of the sample to be clearly seen.

DIFFERENCE FROM THE PRIOR ART

An important difference exists between this prior art and the disclosure herein. Specifically, and as in the prior art, collimation occurs radially of the sample. As will hereafter be set forth, by utilizing a toroidally curved and ruled mirror having two discrete curvatures the ability to examine the sample under chromatically classified light of selected frequency and high intensity is obtained, where diffraction gradients in the sample do not significantly affect sample image scanned.

STATEMENT OF THE PROBLEM

Modern centrifuging techniques require the sensing of stratification of a sample while the sample is being classified. Unfortunately, such samples can be almost entirely opaque. Efficient use of illuminating radiation is required.

Moreover, there is a need to monochromatically scan as well as to vary the frequency of the monochromatic scan. That is to say the wavelength of illumination at which the samples are inspected must be changed. All this must occur in the time domain where sample processing in the centrifuge is occurring. This time domain includes a rotor rotating at speed of 100,000 rpm.

It has been found that prior art optical scanning techniques are not optically sensitive and accurate enough to track some samples, and too complicated, do not have good enough collimation to achieve good spatial scanning resolution, do not operate when a high refraction gradient exists in the sample, and will not operate down to 200 nanometers.

SUMMARY OF THE INVENTION

A centrifuge sample is optically scanned during centrifuging. The sample, placed in a centrifuge rotor having a cell with windows preferably top and bottom windows, is spun until stratification and discrete layering occurs within the sample. Such layers or strata are precisely normal to the radius of the centrifuge at the point of sample and parallel to the spin axis of the centrifuge. Light source is collimated in one plane only. This plane is the sample plane and includes the spin axis of the centrifuge and passes through the sample. The collimated rays pass precisely parallel to the spin axis of the centrifuge across and through layers or strata in the sample. The light is both collimated and chromatically filtered by a toroidal mirror having two curvatures. The cylindrical shape of the mirror with respect to one radius of curvature effects collimation. The rulings of the mirror with respect to the other radius of curvature effect chromatic classification. The light is chromatically filtered and not collimated in the plane perpendicular to the sample plane. A slit scanner having a slit normal to the sample plane transverses the width of the sample below the cell. This traversing slit scanner detects with precision the precise location of the strata in the cell.

A preferred optical path is disclosed including a point source of strobed light of high intensity in the range of 20,000 watts. The point source of light is projected through an aperture 1 mm or less in diameter. This light becomes incident upon a toroidally concave diffraction grating overlying the point of cell sample. The grating is provided with cylindrical sections in the sample plane. The grating acting also as a mirror effects collimation in the sample plane precisely normal to the forming strata in the rotating sample.

Cylindrical section curvature is such that collimation is not effected when the grating is rotated about its axis of rotation. The mirror is ruled as a diffraction grating along lines perpendicular to the sample plane. The sample is strobed by the light at the time of passage of the cell at the sample point. Light from the light source is incident upon the mirror overlying the cell and is chromatically classified. The light passes through the cell in a band of about 5 nanometers to a lower slit scanning detector with an underlying photodetector. The slit scanning detector in combination with the photodetector precisely locates strata forming within the cell during centrifuging.

The mirror can be tilted on an axis included in the plane including the spin axis and radius at the point of sample. This axis of mirror tilt is preferably at right angles to the spin axis of the rotor. The mirror is given unequal spaced rulings so that simple tilt provides the desired chromatic output without the necessity of adjusting the focal length of the mirror with respect to the sample to obtain the chromatically classified light. There results an optical sampling system which can tolerate as much as 4 decades of light attenuation to enable the dynamics of centrifuging to be closely followed at discrete bands requiring high resolution.

It has been found that imaging of the collimated monochromatic light to an examining slit gives enhanced optical analysis immediately adjacent the so-called meniscus for the critical observation of optical density gradients indicating the separation state. By the expedient of constructing a single scanning head which undergoes radial excursion across the appropriate observation windows, a variable chromatic scan having high resistance to artifact is enabled.

OTHER OBJECTS AND ADVANTAGES

An object of this invention is to increase the illumination intensity at a sample undergoing process by spinning in a centrifuge. According to this aspect, an apertured light source is strobed at the instant a sample is to be taken. Light from the light source is incident upon a mirror immediately overlying the sample. The mirror is provided with a preferably cylindrical surface in a plane including the spin axis of the centrifuge and the radius of the sample point. Light is reflected downwardly from the mirror collimated precisely parallel to the spin axis of the centrifuge and in a sample plane including the sample point and the spin axis of the rotor. A slit scanning detector disposed normally to the sample plane has excursion back and forth under the sample. This detector precisely identifies layers of stratification by their optical absorption as they are dynamically formed in the centrifuging process.

An advantage of collimating the scanning light only in the sample plane including the spin axis of the rotor and the sample point is that illumination from the light source is more efficiently used. For example, it is possible to illuminate the sample with ten times that illumination which would be available if the sample was illuminated by a normally collimated beam, the normally collimated beam including collimation transverse of the sample plane.

A further advantage of the scanning system herein disclosed is that an extremely narrow bands may be dynamically tracked while they are classified out of the sample. The sedimentation process of the bands (for example their sedimentation coefficient) can be actively followed.

A further advantage of the disclosed collimation is that it reduces the need for an imaging system to refocus the cell to the plane of the image detector. This allows operation with resolution in steep sample refraction gradients.

A further object of this invention is to disclose an apparatus which enables the sample to be chromatically scanned at different wavelengths during the centrifuging process. According to this aspect of the invention, the mirror is ruled and curved. Preferably the mirror is provided with conventional unequally spaced rulings. These rulings are supplied to obviate the necessity of changing the mirror to sample distance for differing sampling wavelengths.

An advantage of this aspect of the invention is that by simply tilting the mirror on which the light source is incident varies the wavelength of the light scanning the sample.

A further advantage of this ruled mirror is that it preserves the efficient use of light at the sample by avoiding collimation of the light in the plane of the strata formed in the sample. Increased illumination is maintained at the sample.

A further object of this invention is to disclose a folded optical path having a long light path from the source to the sample and a short light path from the sample to the detector.

An advantage of this aspect of the invention is that the sample is examined with large depth of field by almost perfectly parallel light rays regardless of the angular position of the grating. At the same time the sample, once examined, is immediate the detector. Little degradation of the optical image of the sample to the slit detector occurs.

A further object of this invention is to disclose a scanning apparatus that applies focus of the collimated monochromatic beam to an observation slit for precision observation in the area of the sample meniscus during centrifugation. According to this aspect, an optical scanning head having an observation slit is mounted for scanning radial excursion. Focusing optics are provided for relaying a conjugate image of the sample along a plane parallel to the rotor spin axis and normal to the radius of the sample. Preferably, the scanning optics compresses or reduces the scanned sample in the order of $\frac{1}{2}$ actual size with the result precision monochromatic absorption measurement results.

An advantage of this scanning apparatus is that precision observation of the optical absorption gradient can occur immediately adjacent the so-called "meniscus" or vertical liquid interface between the sample and void space in the windowed cell. This enables precision measurement of the critical density gradient parameter immediate to the meniscus.

A further advantage of this scanning apparatus is that it collects scattered light at the sample and reimages that light at the observation slit. Thus, degradations to collimation produces by scattering at the sample are collected and utilized in place of degrading overall instrument optical measurement.

Yet another advantage of the disclosed scanning apparatus is that in compressing the image of the sample, depth of field is gained across the sample at the scanned interface. Accurate planar sample results.

An additional advantage of the scanning optics with image compression is that the entire system is much less subject to artifact. For example, inevitable optic degradation, due to particles on the lens air interface, are maintained as constants in the produced measurement in their inevitable presence instead of being themselves scanned artifacts.

A further advantage of the disclosed optical scanning apparatus is that it is a convenient site for mounting view limiting screens for rejecting light outside of a narrow and preferred 2° light emitting cone. As a result, the disclosed optics maintains a high level of background light rejection.

BRIEF DESCRIPTION OF THE DRAWINGS

Other objects, features and advantages of this invention will be more apparent after referring to the following specification and attached drawings in which:

FIG. 1 is a side elevation of a centrifuge with the optical scanning system of the present invention installed thereto;

FIG. 2 is a plan view of the centrifuge of FIG. 1;

FIG. 3 is a side elevation taken in a plane in which chromatic dispersion can occur by the ruled mirror;

FIG. 4 is an optical schematic illustrating the placement of the mirror for causing precisely parallel rays to scan the sample;

FIG. 5 is an optical schematic of the folded light path utilized with the sample of FIG. 1 illustrating the resolution provided by the optical system here shown.

FIG. 6 is a side elevation broken away illustrating the mechanism for turning the mirror.

FIG. 7 is a side elevation section taken radially at the traversing optical head for precision scan of the sample;

FIG. 8 is a side elevation parallel to the spin axis taken normal to the centrifuge radius showing an expanded view of the optics; and, FIG. 9 is a top plan view down onto the optical scan apparatus illustrating placement of a light rejecting screen for the rejection of background light.

Referring to FIGS. 1 and 2, a so-called "ultracentrifuge" is illustrated. Simply stated, a motor 10 spins a rotor R about an axis A. High speeds are involved. It is not uncommon for rotor R to spin at 100,000 revolutions/minute. As is well known in the art, centrifuging occurs in a vacuum to avoid windage.

A sample is contained within a cell S1. The cell includes an upper window 20 and a lower window 22 permitting light to pass parallel to the spin axis of rotor R. It is through these respective windows that a light sample formed in accordance with the teaching of this invention performs the method of examining sample stratification while centrifuging dynamically occurs.

Regarding the light, a tube T has a light L transmitted as a square pyramid to impinge upon a mirror M. Light from mirror M is reflected down through folded tube T1 and through windows 20, 22 in cell S1 of rotor R. After passing through the respective windows 20, 22, light is incident upon a detector D (see FIG. 2). As will hereinafter be illustrated, detector D is a moving slit capable of having excursion over the radial length of the sample.

Forces produced by the centrifuge typically range between a five thousand (5,000) gravitational fields to a half a million (500,000) gravitational fields. It is the purpose of this invention to intimately examine strata dynamically forming as the process of centrifuging continues. It will be appreciated that cessation of the centrifuging process to observe the sample may well destroy the very result that is attempting to be observed. Specifically, stratification that can occur under the large gravitational fields produced often dissipates by way of diffusion once the large gravity fields are removed.

In the following application, it is necessary to define certain planes. These planes once defined allow the configuration of the optics to be intelligently discussed.

First, the sample is typically disposed at a sample point P when the sample is optically read for stratification. Sample point P lies along a radius 26 from the spin axis A of the centrifuge.

A sample plane includes the spin axis A and the radius 26 extending from the spin axis through the point of sample. This sample plane is the plane in which the light collimation occurs. This same sample plane is the plane of FIG. 4.

It is also necessary to describe a plane at right angles to the sample plane. This plane is the dispersion plane and is the plane along which chromatic dispersion of light occurs. Collimation of light does not occur in the dispersion plane. This dispersion plane is the plane of the illustration of FIG. 3.

Having set forth these respective planes, the function of the specialized optics of this invention can be set forth. This function will include first the collimation of the light to produce the desired examination of the strata along the sample plane. Secondly, the chromatic classification of the light will be discussed with respect to the dispersion plane. Finally, and with reference to FIG. 5, the resolution characteristics of the invention will be set forth.

Referring to FIG. 3, a strobed light source L passes an aperture 28 preferably 1 mm or less in diameter. Light 40 from the light source passes respective tube stops 30 and 32 and is incident upon mirror M.

Referring to FIG. 4, the reader will understand that light source L is not shown. FIG. 4, however, does show light 40 emanating downwardly from mirror M through sample 50 past a slit detector 52 and to and upon a detector D. It will be understood that slit 52 scans underneath the sample 50. In such scanning it will identify strata precisely parallel to spin axis A and normal to the sample plane of FIG. 4.

Mirror M is here shown given a cylindrical shape with respect to light source L in the sample plane of FIG. 4. This cylindrical shape is chosen so that rays 40 are precisely collimated within the plane of FIG. 4 along a path parallel to the spin axis of rotor R. Thus, any classified layers of sediment such as that existing at band B have the collimated rays 40 past precisely parallel to and through the band B.

Mirror M is shaped along one axis for the generation of the collimated rays. Along the other axis, the mirror is provided with a different curvature and differently spaced rulings so that tilting of the mirror produces light of vary color.

Such rulings are known. See Pieuchard et al. U.S. Pat. No. 3,909,134 issued Sept. 30, 1975. Additional relevant prior art relating to the construction of such mirrors may be found in Pieuchard et al. U.S. Pat. No. 3,930,728 issued Jan. 6, 1976; Pieuchard et al. U.S. Pat. 3,721,487 issued Mar. 20, 1973; Laude et al. U.S. Pat. No. 3,942,048 issued Mar. 2, 1976; and, Flamand U.S. Pat. No. 3,628,849 issued Dec. 21, 1971.

Rotation of grating to change wavelength occurs about 30° from normal to the light source. Effective curvature for collimation does not change regardless of grating angle.

The reader will understand that the illustrated optics are preferred. Other optics that collimate the light in the sample plane only can be used. For example combinations of lenses and mirrors could be used.

It will be understood that slit 52 traverses the detector D back and forth along the path indicated by double arrow 54. In such a traverse, detector D will see the differences in the receipt of light as described in Cohen U.S. Pat. No. 3,712,742 issued Jan. 23, 1973.

Some numerical examples can be useful. Specifically light source L is typically a strobed zenon source. At the instant of strobing the light source includes output in the range of 20,000 watts.

Great attenuation of the light can occur through the essentially opaque layers such as band B in sample 50 inside cell S1. Light attenuation on the order of 17 decades ($10^{17}$) overall can occur. Light attenuation at the sample can be 3 decades ($10^3$).

Referring back to the view of FIG. 3, it is also desirable to scan the sample 50 in cell S1 with chromatically classified bands. For example, it is desired to scan proteins being classified in centrifuges in the range of 200 to 800 nanometers or higher (this range being in the ultraviolet and visible portion of the optical spectra). Accordingly, mirror M1 is provided with curvatures having unequal spaced rulings in the plane of FIG. 4. As viewed in FIG. 3, the rulings extend into and out of the plane of the drawing. By the expedient of turning the mirror about an axis 60, as illustrated by arrow 62, scanning of sample 50 can occur in 5 nanometer wide bands. The reader will understand that the width of the scanning optical bands or band pass is in effect determined by the solid angle of mirror radiation defined through windows 20, 22 as viewed in FIGS. 3 and 4.

Serendipity is present from such scanning. Specifically, the band of chromatically classified light is parallel to and in the plane of the band B as shown in FIG. 4. With such an alignment both the band B and its respective surfaces are illuminated with light. The illuminating light is in the order of ten times that light which would be available had the light been collimated with respect to both the planes of FIGS. 3 and 4. By the expedient of restricting collimation to the plane of FIG. 4 and permitting chromatographic classification across the band B in the plane of FIG. 3 over 10 times the light reaches band B in sample S.

Referring to FIG. 5, an optical schematic of the system is illustrated. This schematic demonstrates how the length of the folded light path illustrated in FIGS. 3 and 4 assists in the band resolution of the sample.

It will be seen that the distance $X_1$ represents the effective length of the optical path between the light L and the sample S1. This distance is equal to about 33 cm.

Likewise, the distance $X_2$ is the distance between the slit 52 and the sample S1. This distance is about 2 cm. It will be observed that the folded light path $X_1$ is very much longer than the path $X_4$. Therefore, the slit 52 will see the banding B at a high resolution where:

$$\frac{d_2}{X_2} < \frac{d_1}{X_1}$$

It has been emphasized that it is desirable to rotate mirror M to obtain differing chromatic resolution. Actual apparatus for effecting this rotation is shown in FIG. 6.

Referring to FIG. 6, the optical tube in the vicinity of the mirror schematically shown in FIGS. 3 and 4 is illustrated. The mirror is shown in the same plane as the schematic of FIG. 4.

Specifically, light passes upwardly of tube T. Optical baffles eliminate all portions of the beam from light L (See FIG. 1) save and except that light which will impact mirror M. Light is reflected from mirror M and passes down tube T1 to sample the contents of a rotating cell.

Mirror M pivots about a pivot 102. The mirror is driven in such pivotal motion by a gear train including gears 103, 104. This gear train also includes reduction gears 105, 106, an idler gear 107 which is finally driven by a rack 108. As can be readily understood, by linear motion of rack 108 towards and away from the mirror, finely adjusted and precise rotation of mirror M can occur. Since the mirror always collimates, change in angle of the mirror will only affect the color doing the sampling at the rotating cell.

The reader will appreciate that the ability to rapidly change color enables the rapid adjustment of the color for sampling the classified materials within the cell. Thus, while the photodetector passes over the radius of an individual cell, the color of the sampling light can be rapidly changed for optimum detection of classified strata having varying optical densities.

The alignment of slit 52 and the detector D as shown in FIG. 4 has an additional advantage that is not apparent. Specifically, as sample S1 is increasing classified, various components of the sample will settle out at discrete layers. These components can include various salts.

Unfortunately, such heavier components, especially classified salts, have differing indices of refraction. This being the case, it will be appreciated that for slit 52 to see these bands, an aperture of some angular width must be provided.

Accordingly slit 52 has an active width of approximately 0.1 millimeter and is spaced with respect to the active surface of detector D so that a plus or minus 2 degree from the vertical angular view of the sample is obtained. Using this technique, light that is refracted by the sample with differing indices of refraction can still be observed and all of the stray light beyond this angle does not impinge on the detector.

Having set forth in FIGS. 1-6 an operable embodiment of this invention, an improved optical head H for scanning the cell S1 of this invention is disclosed.

Having simultaneous reference to FIGS. 7 and 8 a rotor R having a sample cell S1 is illustrated. Sample cell S1 includes two sample apertures 200, 201 (see FIG. 8). Respective windows 210, 211 confine fluid interior of the cell S1 to two discrete optical paths. Typically one such optical path including cell 200 includes a reference. An adjacent optical path including cell 201 includes a sample. Typically the reference will include a solvent and a density forming solute for observation. The sample will include the same solvent with the identical solute and have added thereto materials for separation. Typically such materials could include macromolecules. As previously described, tube T emanates collimated monochromatic light downwardly to and through the samples. As here illustrated, the monochromatic light goes through sample cell 201.

Referring to both FIGS. 7 and 8, a scanning head H is shown. Typically, the head is maneuvered to move within the plane of FIG. 7 and into and out of the section of FIG. 8.

Optical head H includes two planoconvex lenses which convex lenses focus a conjugate and compressed image of classification interfaces to an optical slit 240.

Referring to FIG. 8, a section parallel to the spin axis and normal to the radius is shown. This section includes a plane of monochromatic light.

Lenses 236 and 238 are given power to relay a conjugate compressed image across the interface 260 in cell 201 to slit 240. Compression of the image occurs in the order of 50%. Such compression in combination with collimated light gives a depth of field substantially the vertical height of the interface 260 located in cell 201.

Typically, the entire optical head is scanned. It is scanned radially of the cell along path 270.

Referring to FIG. 7 an air solvent interface 260 is illustrated. As those skilled in the centrifuge arts are aware, it is extremely important to be able to measure the optical density gradient up to the interface or "meniscus" 260. It has been found that with the focusing head H such measurements can occur.

Specifically, and even though very careful precaution is taken in the collimation of the light herein, scattering can and does occur when light L passes across the interface 260. By the expedient of having the conjugate image scanning head H, light scattered off the surface of the meniscus 260 is gathered and redirected to the conjugate image at 240. In such gathering, the scattered light is in effect reconstituted to the original absorption pattern so that the intensity measurement taken at slit 240 contains great freedom from artifact introduced at the meniscus.

It should be understood that the type of scan herein is especially free from chromatic aberration. It is known that where scans occurs in the range of 200 and 400 nanometers, lenses become wavelength dependent for their refractive power. Here, however, with the compression of the optical image and movement of lens with the slit, errors of focal length due to changes in lens refraction of the monochromatic light are minimized.

Referring to FIGS. 7, 8 and giving full attention to FIG. 9, can be seen that head H is an ideal mount for an optical screen 272. Screen 272 defines a light rejection aperture 270 which in combination with slit 240 only receives a 2° cone of light from cell S1. This 2° cone of light assures high rejection of background light or light spectrally reflected within the sample which would otherwise degrade the highly sensitive monochromatic measurement enabled by this apparatus. It will thus be appreciated that the focusing head in combination with the collimated and monochromatic scanning light has a unique sensitivity.

With the focusing optics in combination with the monochromatic mirror M1 and its collimated output, the aperture acts as the control for both the band pass of the mirror and the width of the collimated interrogating beam. As can be seen in FIG. 7, the length of the slit is normal to a radius. In the example shown it is in the range of 3 to 5 nanometers of band pass.

The width of the slit is in the order of 50 microns. This is the dimension radially of the interrogating slit at the sample.

It will be remembered that the plan of the sample is in effect imaged to the detector slit. Therefore, the system does not focus in on cell boundaries as artifacts. There is an effective decoupling of error that might otherwise be present in both the dimension of the pie shaped window at the cell as well as any vignetting caused by the rotor in the physical holding of the cell.

What is claimed:

1. A method for optically detecting stratification in a sample while said sample is being spun in a centrifuge, said method comprising the steps of:
    placing said sample in a chamber in a centrifuge rotor spun about an axis, said chamber in said rotor having at least two windows for permitting light to pass through the sample parallel to centrifuge produced stratification at a point of observation;
    providing a light source for observing said sample through said windows while said sample is being spun by said centrifuge rotor;
    providing a toroidal mirror having a first substantially cylindrical radius of curvature for collimating light from said light source parallel to the axis of said rotor only whereby the collimated light passes parallel to said strata and a second radius of curvature intersecting said first radius of curvature;
    ruling said toroidal mirror with respect to said second radius of curvature to chromatically classify light to differing frequencies at differing angularities from said mirror;
    rotating said mirror with respect to said first radius of curvature to maintain collimation and select color of light incident upon said sample;
    providing an optical head for receiving an image of said sample parallel to the axis of said rotor and normal to the radius of said rotor at said chamber;
    providing relay optics for relaying an image of said sample to the optical head;
    providing a slit parallel to the plane of said image;
    and detecting and receiving said light after passage through said chamber at said slit to determine location of stratification by optical absorption in said sample.

2. The method of claim 1 and further including the step of radially scanning said optical head.

3. Apparatus for optically detecting stratification in a sample in a centrifuge rotor while said centrifuge rotor is spun to move said sample past a sample point on a sample plane including the spin axis of said rotor and said sample point, said apparatus comprising:
    a centrifuge rotor for rotation about an axis;
    said rotor defining a chamber having at least two windows for permitting light to pass through the sample parallel to the stratification of said sample at a point of observation;
    a light source for observing said sample through said windows while said sample is being spun by said centrifuge rotor;
    a toroidal mirror having a first and second radius of curvature, said first radius of curvature for collimating light from said light source parallel to the axis of said rotor and in the sample plane only whereby collimated light passes parallel to said stratification; and,
    said toroidal mirror ruled with respect to said second radius of curvature to provide chromatic classification of differing frequencies at differing angles with respect to said mirror;
    means for rotating said mirror about said first radius of curvature to select a frequency of light for examining said sample;
    means for detecting light after said passage through said chamber at said windows to determine stratification of said sample, said means for detecting including:
    a slit aligned normal to a radius from the spin axis of said rotor;
    relay optics mounted between said sample and said slit, said relay optics for relay a conjugate image of said sample to said slit to determine stratification of said sample.

4. The invention of claim 3 wherein said relay optics compress the image of said sample.

5. The invention of claim 3 and further including a screen adjacent said relay optics, said screen in combination with said slit configured for rejection of light to be detected by the means for detecting light.

6. The invention of claim 3 and including means for radially scanning said means for detecting light.

7. The invention of claim 3 and wherein said slit is normal to a radius taken from said sample point through the spin axis of said rotor and the length of said slit determines the band pass of said mirror.

* * * * *